(12) United States Patent
Harandi et al.

(10) Patent No.: US 11,530,173 B2
(45) Date of Patent: Dec. 20, 2022

(54) SELECTIVE OLEFINS PRODUCTION FROM LIGHT PARAFFINS

(71) Applicant: ExxonMobil Technology and Engineering Company, Annandale, NJ (US)

(72) Inventors: Mohsen N. Harandi, Calgary (CA); Randall J. Meyer, Clinton, NJ (US)

(73) Assignee: EXXONMOBIL TECHNOLOGY AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 17/643,867

(22) Filed: Dec. 13, 2021

(65) Prior Publication Data
US 2022/0220045 A1     Jul. 14, 2022

Related U.S. Application Data

(60) Provisional application No. 63/137,364, filed on Jan. 14, 2021.

(51) Int. Cl.
C07C 5/333 (2006.01)
B01J 29/40 (2006.01)
B01J 8/24 (2006.01)

(52) U.S. Cl.
CPC ............... *C07C 5/333* (2013.01); *B01J 8/24* (2013.01); *B01J 29/40* (2013.01); *C07C 2529/40* (2013.01)

(58) Field of Classification Search
CPC ........ C07C 5/333; C07C 2529/40; B01J 8/24; B01J 29/40
See application file for complete search history.

(56) References Cited

U.S. PATENT DOCUMENTS 7,384,883 B2 * 6/2008 Dath ..................... B01J 29/40
                                                      502/85
10,399,913 B2    9/2019 Harandi et al.

* cited by examiner

*Primary Examiner* — Thuan D Dang
(74) *Attorney, Agent, or Firm* — Shook, Hardy & Bacon L.L.P.

(57) ABSTRACT

A method may include: contacting a light paraffin feed comprising ethane, propane, butane, naphtha or combinations thereof with a restrained catalyst in a reactor; converting at least a portion of the light paraffin feed to ethylene, propylene, or combinations thereof with an olefin selectivity of at least 70 wt. % and methane selectivity of less than 15 wt. %; and withdrawing a product stream from the reactor.

8 Claims, 2 Drawing Sheets

SELECTIVE OLEFINS PRODUCTION FROM LIGHT PARAFFINS

CROSS-REFERENCE TO RELATED APPLICATIONS

This application claims the benefit of U.S. Provisional Application No. 63/137,364, filed on Jan. 14, 2021, the entire contents of which are incorporated herein by reference.

FIELD

This application relates to production of olefins from light paraffins, and in particular, embodiments relate to the utilization of a restrained catalyst to convert a paraffinic feed comprising ethane and propane to ethylene and propylene.

BACKGROUND

For decades the chemical industry has been working on refining the process of selective olefins production from low value light paraffins, particularly ethane and propane. The current state of art is steam cracking which provides an ethylene selectivity of about 80% from ethane, with assistance of steam dilution. However, steam cracking is energy intensive as heat input is indirect requiring large size furnaces in parallel and a back-up decoking service. Steam cracking with solid catalyst circulations in a fluid-bed have been developed but to achieve high selectivity to ethylene and propylene, a large amount of steam dilution is used which increases the energy requirements and increased $CO_2$ emissions. Zeolites have also been used to produce light olefins but the selectivity to light olefins has been low and a very significant part of the feed is converted to aromatics and gasoline boiling range components because zeolites are good oligomerization and aromatization catalysts due to their acid sites.

SUMMARY

Disclosed herein are methods and systems for producing olefins from light paraffins. The method may include: contacting a light paraffin feed comprising ethane, propane, butane, naphtha or combinations thereof with a restrained catalyst in a reactor; converting at least a portion of the light paraffin feed to ethylene, propylene, or combinations thereof with an olefin selectivity of at least 70 wt. % and methane selectivity of less than 15 wt. %; and withdrawing a product stream from the reactor.

Disclosed herein is an example system for producing olefins from light paraffins. The system may include a reactor containing a restrained catalyst and an inlet fluidically coupled to a light paraffin feed source, the light paraffin feed source comprising ethane, propane, or combinations thereof; a catalyst regenerator configured to accept spent restrained catalyst from the reactor and regenerate the spent restrained catalyst and wherein the catalyst regenerator is configured to provide regenerated restrained catalyst to the reactor; and a transfer line configured to convey a reactor effluent to a separation unit.

Further disclosed here is another example method that includes introducing a feed comprising at least 80% by weight ethane, propane, or combinations thereof into a riser; contacting the feed with a restrained catalyst in the riser; conveying the feed and the restrained catalyst to a fluidized bed reactor; reacting at least a portion of the feed to form products comprising ethylene, propylene, or combinations thereof; separating at least a portion of the restrained catalyst from the feed and/or the products; and withdrawing an effluent stream from the reactor comprising unreacted feed and the products, herein the reactor operates at a temperature in a range of about 500° C. to about 1000° C., at a pressure in a range of about 200 kPa to about 2100 kPa, and at a weight hourly space velocity in a range of about 0.01 WHSV to about 10 WHSV

BRIEF DESCRIPTION OF THE DRAWINGS

These drawings illustrate certain aspects of the present disclosure and should not be used to limit or define the invention.

DETAILED DESCRIPTION

Figure 1:
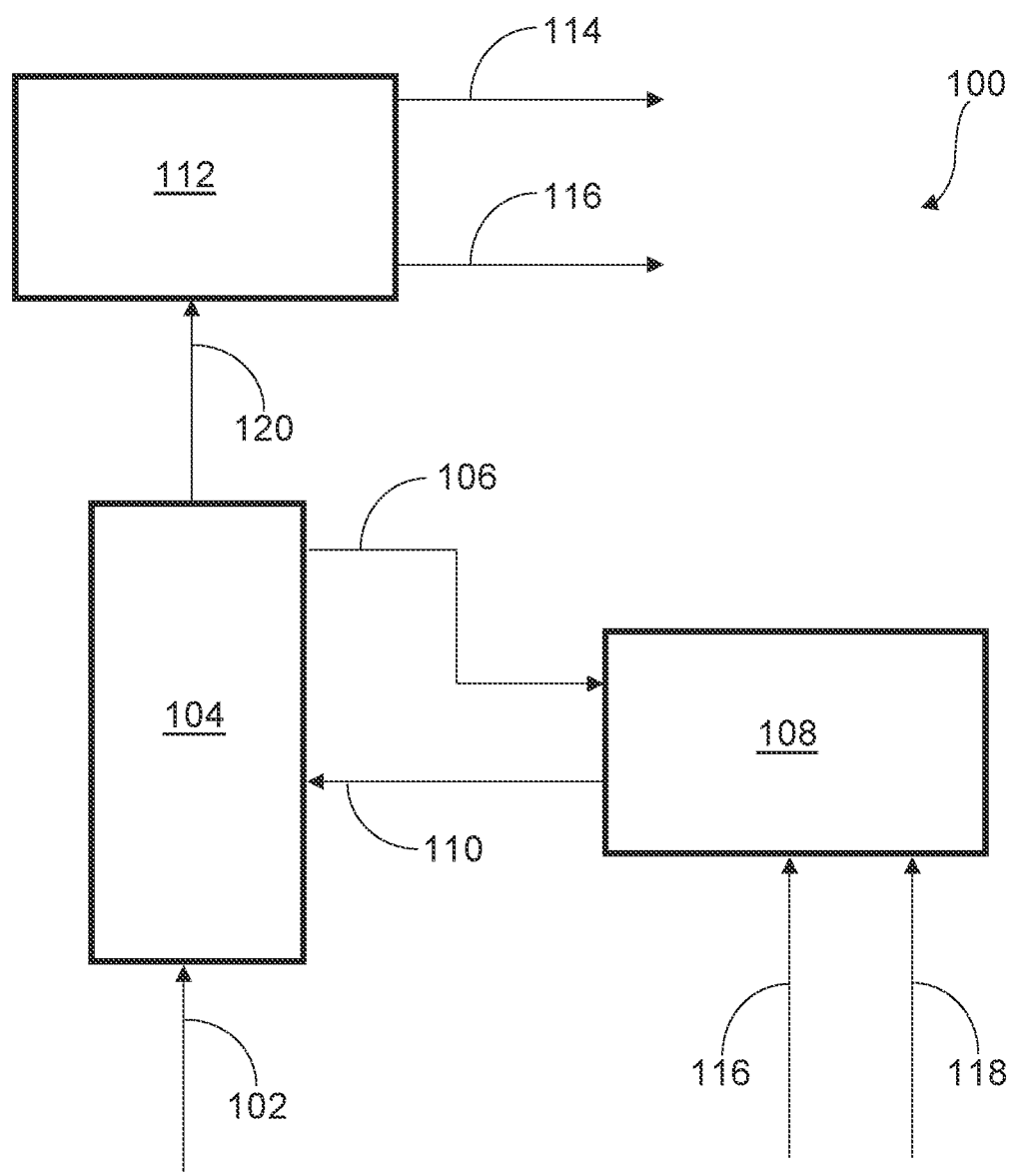
FIG. 1 is a schematic illustration of an integrated system according to one embodiment of the present disclosure for producing for olefins from light paraffins.
Figure 2A:
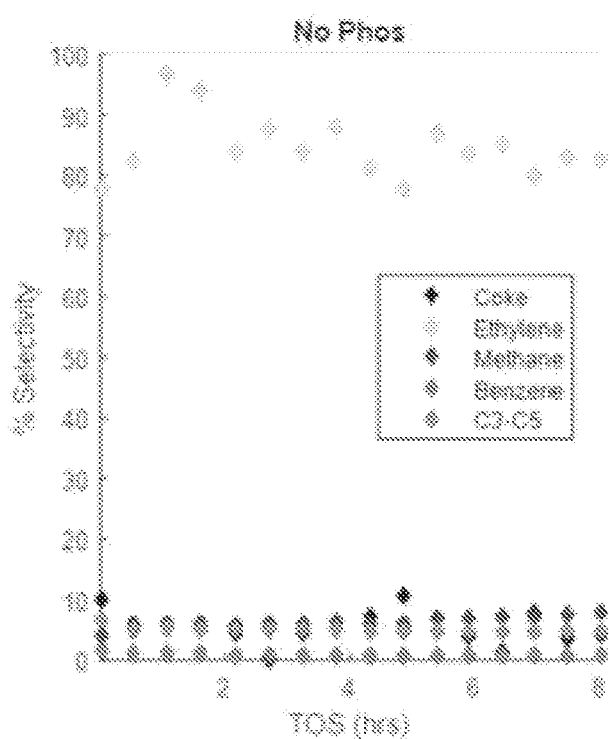
FIG. 2a is plot of results from a HZSM-5 catalyst experiment.
Figure 2B:
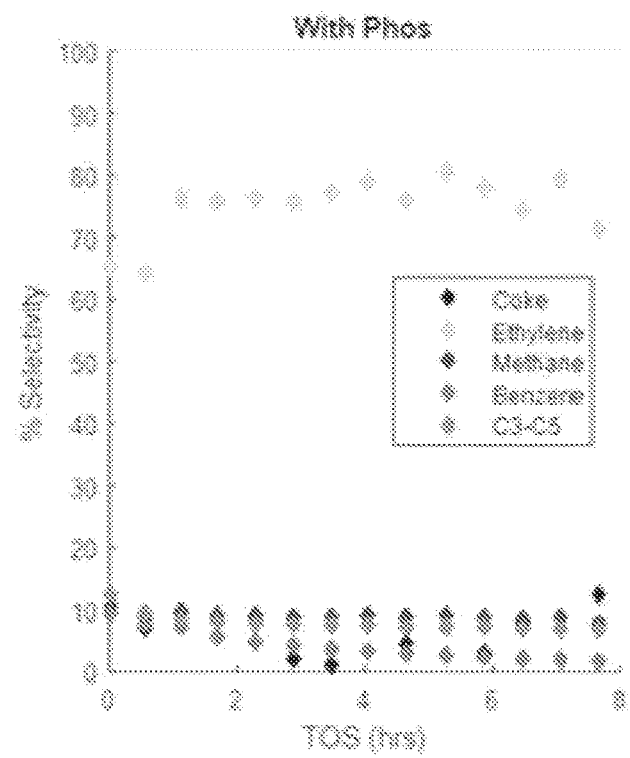
FIG. 2b is plot of results from a PZSM-5 catalyst experiment.

Disclosed herein are methods and systems for producing olefins from light paraffins. The methods and systems disclosed herein may utilize a restrained catalyst where the catalytic activity of the restrained catalyst has been reduced by steaming. The restrained catalyst can convert paraffins to olefins while suppressing the formation of aromatics and gasoline boiling range components such as hydrocarbons with carbon numbers from C5-C10. Using the restrained catalyst in addition to a lower severity reactor operating conditions which may suppress methane and/or coke formation at the expense of per pass conversion. However, the high olefin selectivity of the restrained catalysts, among other advantageous features, allows for the process to be economical even with lower per pass conversion than steam cracking. Another advantageous feature of the present invention may be that the light paraffin feed does not need dilution with steam, or any other diluent, thereby reducing carbon dioxide formation and reducing energy cost associated with the production of light olefins as compared to steam cracking.

The restrained catalysts may have both paraffin dehydrogenation activity and hydrocarbon oligomerization activity. In some embodiments, the same catalyst (or the same mixture of catalysts) is used for to perform all of the hydrocarbon conversion reactions. In a particular embodiment the catalyst is a restrained oligomerization catalyst with a binder and the binder contains some dehydrogenation function. A catalyst for the oligomerization reactions may include an aluminosilicate such as a zeolite. Zeolites suitable for inclusion in the catalyst may include, without limitation, ZSM-5, ZSM-11, ZSM-12, ZSM-22, ZSM-23, ZSM-35, ZSM-38, ZSM-48, ZSM-50, ZSM-57, ZSM-58, MCM-22, MCM-35, MCM-49. MCM-57, SUZ-4, COK-5, ITQ-39, ferrierite, erionite, silica-aluminum phosphate (SAPO), BEA, MOR, FAU, and combinations thereof. Zeolite catalyst may also have paraffin dehydrogenation activity, either naturally, or from one or more metal promoters which may incorporated into the zeolite catalyst to create or enhance paraffin dehydrogenation activity. Some metal promoters may include P, Zn, Ga, Ni, La, Sn, B, Ge, Fe, Co, Cu, Ti, Mo, Ag, Na, Rb, Ba, K, Li, Cs and combinations thereof.

Paraffin dehydrogenation catalysts may include oxides and sulfides of elements from group 4, group 5, group 6, group 7, group 8, group 9, group 10, and mixtures thereof on an inert support such as alumina or silica-alumina. Some exemplary paraffin dehydrogenation catalysts may include, without limitation, sulfides and/or oxides of titanium, zirconium, vanadium, niobium, tantalum, chromium, molybdenum, tungsten, manganese, iron, cobalt, rhodium, iridium, nickel, palladium, platinum and combinations thereof disposed on a support. Any of the oxides or sulfides of group 4, group 5, group 6, group 7, group 8, group 9, or group 10 elements may be exchanged onto any of the above-mentioned zeolites to provide a catalyst having dehydrogenation activity.

The zeolite may be dispersed on a matrix including a binder material such as silica or alumina and an inert filler material such as kaolin. A restrained catalyst may include a zeolite content of about 10 wt. % to about 100 wt. % by weight of the restrained catalyst. Alternatively, the restrained catalyst may include a zeolite content of about 10 wt. % to about 40 wt. %, about 40 wt. % to about 60 wt. %, about 60 wt. % to about 100 wt. %, or any ranges therebetween. When present, the matrix, including a binder material, may be included in an amount of about 10 wt. % to about 100 wt. % by weight of the restrained catalyst. Alternatively, the restrained catalyst may include a matrix and binder content of about 10 wt. % to about 40 wt. %, about 40 wt. % to about 60 wt. %, about 60 wt. % to about 100 wt. %, or any ranges therebetween.

The restrained catalysts may be produced by a process which may include steaming any of the catalysts described above at conditions sufficient to reduce the catalytic activity of the catalyst to a desired level. Any of the above-mentioned catalysts may be steamed at a pressure from about 650 kPa to about 7000 kPa and a temperature of about 200° C. to about 1500° C. The catalysts may be steamed for any amount of time desired to reduce catalytic activity, for example, without limitation from about 1 hour to steaming in excess of 72 hours of steaming. Steaming may also take place at a number of steps running at various temperatures. Catalytic activity as used herein is the increase in rate of a chemical reaction, such as dehydrogenation, caused by the presence of the restrained catalyst. The catalytic activity may be reduced by any amount from about 10% to about 90% as compared to the same catalyst before steaming. Alternatively, the catalytic activity may be reduced by about 10% to about 30%, about 30% to about 60%, about 60% to about 99%, or any amounts there between.

The restrained catalyst may have a relatively high selectivity at reactor operating conditions to olefin production over other reactions such as cracking, coking, and oligomerization. Catalyst selectivity should be understood to mean a ratio of products obtained from given reactants. In some examples, the restrained catalyst may have greater than 50% selectivity to olefin production. Alternatively, the restrained catalyst may have greater than 60% selectivity to olefin production, greater than 70% selectivity to olefin production, greater than 80% selectivity to olefin production, or greater than 90% selectivity to olefin production. The relatively high selectivity to olefins combined with the relatively lower activity of the restrained catalyst may economically allow the reactor containing the restrained catalyst to operate at lower temperatures than steam cracking which in turn reduces methane and coke production. Another advantage of the restrained catalyst is that the ability to oligomerize a portion of the feed or intermediate products to $C_5+$ oligomers (hydrocarbons with 5 or more carbons) thus increasing the value of the effluent stream while shifting the olefins and paraffins reaction equilibrium.

Any paraffin feed containing ethane, propane, butane, naphtha, or combinations thereof may be utilized in the methods and systems described herein. Other components of the paraffin feed may include methane, ethylene, propylene, and $C_5$-$C_{14}$ paraffins and/or olefins. Exemplary paraffin feeds are those in the $C_2$-$C_{10}$ range, or the $C_2$-$C_5$ range, especially $C_2$-$C_5$ paraffins, such as ethane and propane. The paraffin feed may include at least about 10 wt. % to about 100 wt. % $C_2$-$C_5$ paraffins. Alternatively, the paraffin feed may include at least about 10 wt. % to about 30 wt. % $C_2$-$C_5$ paraffins, about 30 wt. % to about 60 wt. % $C_2$-$C_5$ paraffins, about 60 wt. % to about 90 wt. % $C_2$-$C_5$ paraffins, about 90% to about 100% $C_2$-$C_5$ paraffins, or any ranges there between. The paraffin feed may be from any source containing suitable amounts of the paraffins as described above. Some non-limiting feeds may include low value refinery streams, such as refinery fuel gas or flue gas from a cracking or coking process, for example FCC fuel gas. Other feeds may include a feed from a distillation column such as atmospheric distillation, a cracking unit, or a paraffinic LPG and/or any fraction of light naphtha, for example light FCC naphtha.

When utilizing the restrained catalysts disclosed herein, no steam dilution may be necessary to achieve selectivity to olefins. However, while not necessary to the present systems and methods, steam dilution may still be utilized if desired. For example, without limitation, the paraffin feed may be diluted with about 0.01 wt. % to about 0.5 wt. % steam, if desired. Alternatively, the paraffin feed may be diluted with about 0.01 wt. % to about 0.1 wt. % steam, about 0.1 wt. % to about 0.2 wt. % steam, about 0.2 wt. % to about 0.3 wt. % steam, about 0.3 wt. % to about 0.4 wt. % steam, about 0.4 wt. % to about 0.5 wt. % steam, or any ranges therebetween.

Any suitable reactor type may be utilized in the methods and system described herein. Some exemplary reactor types may include, without limitation, fixed bed reactors, trickle-bed reactors, moving bed reactors, rotating bed reactors, fluidized bed reactors, riser reactors, and slurry reactors. The reactor operating conditions such as pressure, temperature, and weight hourly space velocity may be selected such that the effluent from the reactor contains products in the desired mass fraction or to meet other operational objectives such as per pass conversion, energy use, or coke make, for example. As discussed above, the restrained catalyst may allow for relatively lower severity operating conditions as compared to stream cracking, at the expense of lower per pass conversion but with higher overall selectivity to the desired olefin products. Suitable reactor pressures may be in the range of from about 200 kPa to about 10000 kPa. Alternatively, the reactor may be operated at a pressure in a range of from about 200 kPa to about 500 kPa, about 500 kPa to about 1000 kPa, about 1000 kPa to about 1500 kPa, about 1500 kPa to about 2100 kPa, about 2100 kPa to about 5000 kPa, about 5000 kPa to about 7500 kPa, about 7500 kPa to about 10000 kPa, or any ranges therebetween. Suitable reactor temperatures may be in the range of from about 500° C. to about 1000° C. Alternatively, the reactor may be operated at a temperature in a range of from about 500° C. to about 600° C., about 600° C. to about 700° C., about 700° C. to about 800° C., about 800° C. to about 900° C., about 900° C. to about 1000° C., or any ranges therebetween. Suitable reactor weight hourly space velocities may be in the range of from about 0.2 WHSV to about 20 WHSV. Alternatively, the reactor may be operated at a weight hourly space velocity of about 0.2 WHSV to about 1 WHSV, about 1 WHSV to about 3 WHSV, about 3 WHSV to about 5 WHSV, about 5 WHSV to about 7 WHSV, about 7 WHSV to about 10 WHSV, about 10 WHSV to about 15 WHSV, about 15 WHSV to about 20 WHSV or any ranges therebetween.

In reactors where the restrained catalyst is utilized, the coke production may be relatively low and regenerating the catalyst, by oxidizing the coke for example, to produce carbon dioxide and heat may not provide enough energy to sustain the reaction. In some examples, a separate fuel stream may be utilized which provides the heat necessary to sustain the reaction. The fuel stream may be any fuel stream which can provide energy to the reactor, including, but not limited to, refinery fuel gas, hydrogen sulfide, methane, ethane, propane, vacuum residue, atmospheric residue, petroleum coke, and combinations thereof. Of particular interest may be fuels with low hydrogen to carbon ratios (H/C ratio). As discussed above, the reactor may operate at relatively higher pressures, as compared to stream cracking furnaces, due to the selection of the restrained catalyst. High pressure reaction section operation may allow more economical capture of carbon dioxide from reactor effluent as acid gas treatment units, including amine units and other units configured to treat $H_2S$ and/or carbon dioxide, advantageously operate at relatively higher pressures than atmospheric thereby eliminating or reducing compression requirements for treatment of the reactor effluent. In addition, higher pressure operations allow lower cost separation of the products and the recycle stream. An advantage of fluid-bed operation is that fuels with low hydrogen to carbon ratios may be utilized since fuels with low hydrogen to carbon ratios produce a purer stream of carbon dioxide when burned than fuels with relatively higher hydrogen to carbon ratios.

Paraffin dehydrogenation and oligomerization conditions employed in the present process broadly include temperatures of about 500° C. to about 1000° C., pressures of about 200 kPa to about 10000 kPa, WHSV of 0.2 WHSV to about 20 WHSV. The space velocity required to achieve the desired extent of dehydrogenation will depend upon, among other factors, the feed composition and the temperature of the catalyst. The paraffin dehydrogenation and oligomerization reactions may be conducted in any reaction zone, including a riser reactor, a fluid bed reactor, or any other reactors discussed above. Additionally, the paraffin conversion reactions may be conducted in a transfer line used to supply the freshly regenerated catalyst from a regeneration zone to the reactor. A series of chemical reactions, including, but not limited to dehydrogenation, oligomerization, isoparaffin/olefin alkylation, and aromatization, may occur in any of the reaction zones thereby converting the paraffin feed to a mixture of olefins, $C_4+$ oligomers, and aromatic hydrocarbons.

Where a feed comprising light paraffins (primarily ethane and propane) is utilized with the restrained catalyst, the major product of the methods and systems described herein is a product stream comprising primarily ethylene and propylene. However, additional side products such as coke, methane, hydrogen, as well as $C_4+$ products, including aromatics, may also be present in the reactor effluent, the specific ratios of each being determined by the chemical identity of the restrained catalyst and reactor operating conditions. The reactor may be operated in such as manner as to produce any desired per pass conversion of the feed. Some exemplary per pass conversion may be from about 20% per pass conversion to about 70% per pass conversion. Alternatively, from about 20% per pass conversion to about 25% per pass conversion, about 25% per pass conversion to about 30% per pass conversion, about 30% per pass conversion to about 40% per pass conversion, about 40% per pass conversion to about 50% per pass conversion, about 50% per pass conversion to about 70% per pass conversion, or any ranges there between. However, it should be noted that for a restrained catalyst as described herein, relatively higher weight hourly space velocities and relatively lower temperatures may produce a higher olefins selectivity than the same catalyst at relatively lower weight hourly space velocity and relatively higher temperature. Furthermore, operating at a higher pressure allows further reduction of temperature and weight hourly space velocity at constant conversion. As such, an important aspect of the present process is that, unlike steam cracking of naphtha, LPG, ethane, or propane, the restrained catalyst allows production of $C_4+$ products including branched aromatics which have a higher commercial value than side products such as methane which is produced in relatively large amounts from steam cracking. It should be noted that in this disclosure production of C4+ is controlled by operating conditions to avoid having C4− olefin selectivity of less than 60%. One parameter may be to maximize conversion without producing too much methane using an advantageously tailored catalyst as described above. Methane selectivity can be below 9 wt. %. Another differentiating feature of the present application over existing fluidized catalytic cracking of naphtha or other relatively heavier hydrocarbon feeds to produce propene is that the light paraffin feed may consist almost entirely of ethane, propane, or combinations thereof with only trace amounts of other hydrocarbons present in the feed. The catalysts used in on-purpose FCC propylene production require longer chain naphtha range hydrocarbon in the feed and therefore very little of ethane and propane in the feed would react to form ethylene and propylene. If in the conventional process for naphtha cracking temperature is increased to allow ethane and propane conversion, then the product selectivity is adversely impacted and by products like methane significantly impact the process economics.

FIG. 1 illustrates an exemplary process 100 where a feed comprising light paraffins is dehydrogenated to form an effluent comprising olefins corresponding to the light paraffins. Process 100 may begin by introducing feed 102 comprising paraffins into reactor 104 containing a restrained catalyst and contacting feed 102 with the restrained catalyst within reactor 104. Feed 102 may be any of the previously described feeds which contain ethane, propane, or combinations thereof. Reactor 104 may include any of the previously described reactor configurations, including fixed bed, fluidized bed, or any other reactor design. The reactor pressure and temperature conditions may be selected such that at least a portion of the light paraffins in feed 102 convert to the corresponding olefins. Any of the previously disclosed reactor conditions may be utilized in process 100 to produce a reactor effluent containing the product species in the desired concentrations. The reactor effluent may be transferred through transfer line 120. Transfer line 120 comprising the generated olefins and unreacted light paraffins may be sent to separation unit 112 which may include separation equipment such as distillation columns which may fractionate the reactor effluent into product stream 114 comprising the generated olefins and recycle stream 116 which may comprise the unreacted reactants. Recycle stream 116 may be recycled back in process 100, for example by combination with feed 102 before entering reactor 104.

In examples where catalyst regeneration is desired, a catalyst regenerator 108 may be utilized to regenerate the restrained catalyst. The restrained catalyst may become deactivated either by coke deposition or other means which may require regeneration to regain catalytic activity. Spent catalyst stream 106 may be withdrawn from reactor 104 and introduced into catalyst regenerator 108 whereby the spent catalyst may be contacted with oxygen containing stream 116 to oxidize at least a portion of the coke deposit on the spent restrained catalyst. Optionally, fuel gas stream 118 containing a combustible material may also be introduced into regenerator 108 which may provide additional energy to reactor 104, if required. Regenerated catalyst stream 110 comprising regenerated restrained catalyst may be introduced into reactor 104 as shown or, optionally, into feed 102.

Accordingly, the preceding description describes apparatus, systems, and methods for converting light paraffins to olefins utilizing a restrained catalyst. The apparatus, systems, and methods disclosed herein may include any of the various features disclosed herein, including one or more of the following embodiments.

Embodiment 1. A method comprising: contacting a light paraffin feed comprising ethane, propane, butane, naphtha or combinations thereof with a restrained catalyst in a reactor; converting at least a portion of the light paraffin feed to ethylene, propylene, or combinations thereof with an olefin selectivity of at least 70 wt. % and methane selectivity of less than 15 wt. %; and withdrawing a product stream from the reactor.

contacting a light paraffin feed comprising ethane, propane, or combinations thereof with a restrained catalyst in a reactor; converting at least a portion of the light paraffin feed to ethylene, propylene, or combinations thereof; and withdrawing a product stream from the reactor.

Embodiment 2. The method of embodiment 1 wherein the light paraffin feed contains greater than 80% by weight ethane, propane, or combinations thereof.

Embodiment 3. The method of any of embodiments 1-2 wherein the restrained catalyst comprises a zeolite, wherein the zeolite has been steamed to reduce catalytic activity of the zeolite.

Embodiment 4. The method of embodiment 3 wherein the zeolite is selected from the group consisting of ZSM-5, ZSM-11, ZSM-12, ZSM-22, ZSM-23, ZSM-35, ZSM-38, ZSM-48, ZSM-50, ZSM-57, ZSM-58, MCM-22, MCM-35, MCM-49. MCM-57, SUZ-4, COK-5, ITQ-39, ferrierite, erionite, silica-aluminum phosphate (SAPO), BEA, MOR, FAU, and combinations thereof.

Embodiment 5. The method of embodiment 3 wherein the zeolite further comprises a promoter selected from the group consisting of P, Zn, Ga, Ni, La, Sn, B, Ge, Fe, Co, Cu, Ti, Mo, Ag, Na, Rb, Ba, K, Li, Cs and combinations thereof.

Embodiment 6. The method of embodiment 3 wherein the zeolite further comprises an oxide, a sulfide, or combinations thereof of at least one element selected from group 4, group 5, group 6, group 7, group 8, group 9, group 10, and combinations thereof.

Embodiment 7. The method of embodiment 3 wherein the catalyst further comprises alumina, silica-alumina, or both alumina and silica-alumina.

Embodiment 8. The method of any of embodiments 2-6 wherein the reactor comprises a fixed bed reactor, a trickle-bed reactor, a moving bed reactor, a rotating bed reactor, a fluidized bed reactor, a riser reactor, or a slurry reactor.

Embodiment 9. The method of any of embodiments 2-7 wherein the reactor is operated at a temperature in a range of about 500° C. to about 1000° C.

Embodiment 10. The method of any of embodiments 2-8 wherein the reactor is operated at a pressure in a range of 200 kPa to about 10000 kPa.

Embodiment 11. The method of any of embodiments 2-9 wherein the reactor is operated at a weight hourly space velocity in a range of 0.2 WHSV to about 20 WHSV.

Embodiment 12. A system comprising: a reactor containing a restrained catalyst and an inlet fluidically coupled to a light paraffin feed source, the light paraffin feed source comprising ethane, propane, or combinations thereof; a catalyst regenerator configured to accept spent restrained catalyst from the reactor and regenerate the spent restrained catalyst and wherein the catalyst regenerator is configured to provide regenerated restrained catalyst to the reactor; and a transfer line configured to convey a reactor effluent to a separation unit.

Embodiment 13. The system of embodiment 12 wherein the restrained catalyst comprises a zeolite, wherein the zeolite has been steamed to reduce catalytic activity of the zeolite.

Embodiment 14. The system of embodiment 13 wherein the zeolite is selected from the group consisting of ZSM-5, ZSM-11, ZSM-12, ZSM-22, ZSM-23, ZSM-35, ZSM-38, ZSM-48, ZSM-50, ZSM-57, ZSM-58, MCM-22, MCM-35, MCM-49. MCM-57, SUZ-4, COK-5, ITQ-39, ferrierite, erionite, silica-aluminum phosphate (SAPO), BEA, MOR, FAU, and combinations thereof.

Embodiment 15. The system of embodiment 13 wherein the zeolite further comprises a promoter selected from the group consisting of P, Zn, Ga, Ni, La, Sn, B, Ge, Fe, Co, Cu, Ti, Mo, Ag, Na, Rb, Ba, K, Li, Cs and combinations thereof.

Embodiment 16. The system of embodiment 13 wherein the zeolite further comprises an oxide, a sulfide, or combinations thereof of at least one element selected from group 4, group 5, group 6, group 7, group 8, group 9, group 10, and combinations thereof.

Embodiment 17. The system of embodiment 13 wherein the reactor is configured to operate at a temperature in a range of about 500° C. to about 1000° C. and at a pressure in a range of 200 kPa to about 10000 kPa.

Embodiment 18. The method of embodiment 13 wherein the reactor is operated at a weight hourly space velocity in a range of 0.2 WHSV to about 20 WHSV.

Embodiment 19. A method comprising: introducing a feed comprising at least 80% by weight ethane, propane, or combinations thereof into a riser; contacting the feed with a restrained catalyst in the riser; conveying the feed and the restrained catalyst to a fluidized bed reactor; reacting at least a portion of the feed to form products comprising ethylene, propylene, or combinations thereof; separating at least a portion of the restrained catalyst from the feed and/or the products; and withdrawing an effluent stream from the reactor comprising unreacted feed and the products, wherein the reactor operates at a temperature in a range of 500° C. to about 1000° C., at a pressure in a range of 200 kPa to about 10000 kPa, and at a weight hourly space velocity in a range of 0.2 WHSV to about 20 WHSV.

Embodiment 20. The method of embodiment 19 wherein the restrained catalyst comprises a zeolite selected from the group consisting of ZSM-5, ZSM-11, ZSM-12, ZSM-22, ZSM-23, ZSM-35, ZSM-38, ZSM-48, ZSM-50, ZSM-57, ZSM-58, MCM-22, MCM-35, MCM-49. MCM-57, SUZ-4, COK-5, ITQ-39, ferrierite, erionite, silica-aluminum phosphate (SAPO), BEA, MOR, FAU, and combinations thereof, a promoter selected from the group consisting of P, Zn, Ga, Ni, La, Sn, B, Ge, Fe, Co, Cu, Ti, Mo, Ag, Na, Rb, Ba, K, Li, Cs and combinations thereof, and an oxide, a sulfide, or combinations thereof of at least one element selected from group 4, group 5, group 6, group 7, group 8, group 9, group 10, and combinations thereof, wherein the zeolite has been steamed to reduce catalytic activity of the zeolite.

EXAMPLES

To illustrate certain aspects of the systems and methods described herein, an experiment was performed using a HZSM-5 catalyst and PZSM-5 catalyst. The HZSM-5 catalyst and PZSM-5 catalyst were steamed using the techniques discussed above. A reactor was individually charged with the catalysts and a feed containing ethane and propane was charged to the reactor. The reactor conditions were set at 1 WHSV (weighted hourly space velocity), 5 Psig (19.7 Psia), and 725° C. The reactor effluent was monitored via gas chromatography-mass spectrometry for a period of 8 hours, time on stream (TOS). The results of the experiment are shown in FIG. 3a for HZSM-5 and in FIG. 3b for PZSM-5. It was observed that PZSM-5 exhibited lower selectivity than HZSM-5. Further, PZSM-5 was observed to be more active for hydrogen transfer, aromatization, and oligomerization reactions than HZSM-5.

While the invention has been described with respect to a number of embodiments and examples, those skilled in the art, having benefit of this disclosure, will appreciate that other embodiments can be devised which do not depart from the scope and spirit of the invention as disclosed herein. Although individual embodiments are discussed, the invention covers all combinations of all those embodiments.

While compositions, methods, and processes are described herein in terms of "comprising," "containing," "having," or "including" various components or steps, the compositions and methods can also "consist essentially of" or "consist of" the various components and steps. The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the invention, additionally, they do not exclude impurities and variances normally associated with the elements and materials used.

The phrase "major amount" or "major component" as it relates to components included within the renewable diesel of the specification and the claims means greater than or equal to 50 wt. %, or greater than or equal to 60 wt. %, or greater than or equal to 70 wt. %, or greater than or equal to 80 wt. %, or greater than or equal to 90 wt. % based on the total weight of the thermal management fluid. The phrase "minor amount" or "minor component" as it relates to components included within the renewable diesel of the specification and the claims means less than 50 wt. %, or less than or equal to 40 wt. %, or less than or equal to 30 wt. %, or greater than or equal to 20 wt. %, or less than or equal to 10 wt. %, or less than or equal to 5 wt. %, or less than or equal to 2 wt. %, or less than or equal to 1 wt. %, based on the total weight of the thermal management fluid. The phrase "substantially free" or "essentially free" as it relates to components included within the renewable diesel of the specification and the claims means that the particular component is at 0 weight % within the renewable diesel, or alternatively is at impurity type levels within the renewable diesel (less than 100 ppm, or less than 20 ppm, or less than 10 ppm, or less than 1 ppm).

All numerical values within the detailed description and the claims herein modified by "about" or "approximately" with respect the indicated value are intended to take into account experimental error and variations that would be expected by a person having ordinary skill in the art.

For the sake of brevity, only certain ranges are explicitly disclosed herein. However, ranges from any lower limit may be combined with any upper limit to recite a range not explicitly recited, as well as ranges from any lower limit may be combined with any other lower limit to recite a range not explicitly recited, in the same way, ranges from any upper limit may be combined with any other upper limit to recite a range not explicitly recited.

The invention claimed is:

1. A method comprising:
   contacting a light paraffin feed comprising ethane, propane, butane or combinations thereof with a restrained catalyst in a reactor;
   converting at least a portion of ethane, propane, butane or combination thereof to ethylene, propylene, or combinations thereof with an olefin selectivity of at least 70 wt. % and methane selectivity of less than 15 wt. %; and
   withdrawing a product stream from the reactor; wherein the restrained catalyst comprises a zeolite, wherein the zeolite has been steamed to reduce catalytic activity of the zeolite; wherein the light paraffin feed contains greater than 80% by weight ethane, propane, or combinations thereof; wherein the zeolite is selected from the group consisting of ZSM-5, ZSM-11, ZSM-12, ZSM-22, ZSM-23, ZSM-35, ZSM-38, ZSM-48, ZSM-50, ZSM-57, ZSM-58, MCM-22, MCM-35, MCM-49, MCM-57, SUZ-4, COK-5, ITQ-39, ferrierite, erionite, silica-aluminum phosphate (SAPO), BEA, MOR, FAU, and combinations thereof.

2. The method of claim 1 wherein the zeolite further comprises a promoter selected from the group consisting of P, Zn, Ga, Ni, La, Sn, B, Ge, Fe, Co, Cu, Ti, Mo, Ag, Na, Rb, Ba, K, Li, Cs, and combinations thereof.

3. The method of claim 1 wherein the zeolite further comprises an oxide, a sulfide, or combinations thereof of at least one element selected from the group consisting of group 4, group 5, group 6, group 7, group 8, group 9, group 10, and combinations thereof.

4. The method of claim 1 wherein the catalyst further comprises alumina, silica-alumina, or both alumina and silica-alumina.

5. The method of claim 4 wherein the reactor comprises a fixed bed reactor, a trickle-bed reactor, a moving bed reactor, a rotating bed reactor, a fluidized bed reactor, a riser reactor, or a slurry reactor.

6. The method of claim 4 wherein the reactor is operated at a temperature in a range of about 500° C. to about 1000° C.

7. The method of claim 4 wherein the reactor is operated at a pressure in a range of about 200 kPa to about 10000 kPa.

8. The method of claim 4 wherein the reactor is operated at a weight hourly space velocity in a range of about 0.2 WHSV to about 20 WHSV.

* * * * *